US008148095B2

(12) United States Patent
Snyder et al.

(10) Patent No.: US 8,148,095 B2
(45) Date of Patent: Apr. 3, 2012

(54) METHODS FOR PREDICTING PSYCHOTROPIC DRUGS WHICH ELICIT WEIGHT GAIN

(75) Inventors: Solomon H. Snyder, Baltimore, MD (US); Alex Huang, Baltimore, MD (US); Cory Teuscher, South Burlington, VT (US); Sangwon Kim, Baltimore, MD (US)

(73) Assignees: The Johns Hopkins University, Baltimore, MD (US); The University of Vermont College of Medicine, Burlington, VT (US)

( * ) Notice: Subject to any disclaimer, the term of this patent is extended or adjusted under 35 U.S.C. 154(b) by 0 days.

(21) Appl. No.: 12/441,986

(22) PCT Filed: Sep. 10, 2007

(86) PCT No.: PCT/US2007/019617
§ 371 (c)(1),
(2), (4) Date: Jul. 22, 2009

(87) PCT Pub. No.: WO2008/036175
PCT Pub. Date: Mar. 27, 2008

(65) Prior Publication Data
US 2009/0304596 A1 Dec. 10, 2009

Related U.S. Application Data

(60) Provisional application No. 60/845,505, filed on Sep. 19, 2006.

(51) Int. Cl.
G01N 33/53 (2006.01)
G01N 33/542 (2006.01)
G01N 33/567 (2006.01)
G01N 33/566 (2006.01)

(52) U.S. Cl. ........ 435/7.91; 435/7.92; 435/7.9; 435/7.8; 435/7.21; 436/501; 436/503

(58) Field of Classification Search .................. None
See application file for complete search history.

(56) References Cited

OTHER PUBLICATIONS

Theisen et al. No evidence for binding of clozapine, olanzapine or haloperidol to selected receptors involved in body weight regulation. The Pharmacogenomics Journal. 2007 Sep. 2006. 7, 275-281.
Andersson et al. AMP-activated Protein Kinase plays a role in the control of food intake. The Journal of Biological Chemistry, 2004. 279, 12005-12008.
Correll et al. Pharmacogenetics of antipsychotic-induced weight gain. Pharmacology. 2004. 174,477-489.
International Search Report of International application No. PCT/US2007/019617.

*Primary Examiner* — Olga N Chernyshev
(74) *Attorney, Agent, or Firm* — Banner & Witcoff, Ltd

(57) ABSTRACT

The atypical antipsychotic drugs (AAPDs) have markedly enhanced the treatment of schizophrenias but their use has been hindered by the major weight gain elicited by some AAPDs. We found that orexigenic AAPDs potently and selectively activate hypothalamic AMP kinase (AMPK), an action abolished in mice with deletion of histamine H1 receptors. These findings afford a means of developing better therapeutic agents and provide insight into the hypothalamic regulation of food intake.

16 Claims, 11 Drawing Sheets

A.

B.

C.

D.

METHODS FOR PREDICTING PSYCHOTROPIC DRUGS WHICH ELICIT WEIGHT GAIN

This invention was made using funds from the U.S. government. Therefore, the U.S. government retains certain rights in the invention under the terms of US Public Health Service grant DA000266, Research Scientist Award DA00074, and National Institutes of Health Grants NS36526, AI4515, AI41747, and AI45666.

TECHNICAL FIELD OF THE INVENTION

This invention is related to the area of psychotropic drugs. In particular, it relates to screening for orexigenic properties of such drugs.

BACKGROUND OF THE INVENTION

The antipsychotic actions of classic neuroleptics revolutionized the therapy of schizophrenia, but their use has been impeded by side effects such as extrapyramidal symptoms, tardive dyskinesia, a high incidence of non-responders, and the failure of negative symptoms such as apathy to respond. The atypical antipsychotic drugs (AAPDs), pioneered by clozapine, represent an important advance improving negative symptoms, benefiting patients who do not respond to the typical drugs, and displaying fewer side effects (1-5). A major limitation of AAPDs is pronounced weight gain predominantly mediated by increased food intake (6-10).

Weight gain elicited by AAPDs is primarily related to increased food intake though there may also be metabolic alterations (12-14). To directly address central systems that mediate appetite and weight gain we have explored phosphorylation of hypothalamic AMPK, which activates the enzyme (15, 16). Hypothalamic AMPK has been linked to the regulation of food intake (11). In the periphery, AMPK activation is associated with decreased lipid formation, as AMPK phosphorylates acetyl-CoA carboxylase (ACC) inhibiting the generation of malonyl-CoA. Malonyl-CoA is a substrate for fatty acid synthase so that inhibition of ACC diminishes formation of fatty acids and lipid (15-17). In the hypothalamus, AMPK acts in a seemingly reciprocal fashion to regulate food intake (16, 18-20). Kahn and collaborators (11) showed that AMPK activity in the arcuate and paraventricular hypothalamic nuclei is inhibited by anorexigenic agents such as leptin and augmented by the orexigenic agouti-related protein (AGRP) (11).

There is a continuing need in the art to identify and develop more effective drugs with fewer side effects so that patient compliance will increase.

SUMMARY OF THE INVENTION

According to one embodiment of the invention a method is provided for predicting whether an agent which is a psychotropic drug or a candidate psychotropic drug will be orexigenic. The agent is contacted with a histamine $H_1$ receptor (H1R) and one determines if the agent binds to the H1R or inhibits histamine binding to the H1R. The agent is separately contacted with a hypothalamic adenosine monophosphate kinase (AMPK) and one determines if the agent increases phosphorylation or increases activity of the AMPK. The agent is identified as likely to be orexigenic when it (a) binds to H1R or inhibits histamine binding to H1R, and (b) increases phosphorylation of hypothalamic AMPK or increases hypothalamic AMPK activity.

Another embodiment of the invention provides a different method of predicting whether an agent which is a psychotropic drug or a candidate psychotropic drug will be orexigenic. The agent is contacted with an isogenic pair of hypothalamic cells comprising a first and a second cell. The first cell is deficient in histamine type I receptor (HIR) and the second cell is wild-type for histamine type I receptor. One determines if the agent increases phosphorylation or increases activity of hypothalamic AMPK in the first and second cells. One identifies the agent as likely to be orexigenic when it increases phosphorylation of hypothalamic AMPK or increases hypothalamic AMPK activity in the second cell to a significantly greater extent than in the first cell.

These and other embodiments which will be apparent to those of skill in the art upon reading the specification provide the art with methods of identifying drugs and candidate drugs which will have fewer adverse effects.

BRIEF DESCRIPTION OF THE DRAWINGS

(FIG. 1A and FIG. 1B) Hypothalamic slices were incubated in oxygenated artificial cerebrospinal fluid buffer with 500 nM drugs for 30 min. Phospho-AMPK (AMPK-P) and total AMPK were detected by Western blotting. (FIG. 1C and FIG. 1D) Hypothalamic slices were incubated with 500 and 500 mM clozapine or olanzapine for various times as indicated in the figure. Phospho-AMPK and total AMPK were detected by western blotting. (FIG. 1E and FIG. 1F) Hypothalamic slices were incubated with different concentrations of clozapine or olanzapine for 30 min. $\alpha 2$-APMK enzymatic activity was measured with SAMS peptides as a substrate.

(FIG. 2A and FIG. 2B) Mice received clozapine (1 or 5 mg/kg) and were sacrificed at 3 h. Hypothalami were removed and tissue lysates analyzed for phospho-AMPK or $\alpha 2$-AMPK activity. (FIG. 2C and FIG. 2D) Mice received clozapine (1 or 5 mg/kg) and were sacrificed at 3 h. Different parts of brain were isolated and $\alpha 2$-AMPK activity was assayed. Bars represent the mean±SE of three independent lysates performed in triplicate. (* Student's t-test, n=5)

(FIG. 3A) Hypothalamic slices were incubated with different concentration of leptin in the absence or presence of 50 nM clozapine for 30 min. Phospho-AMPK and total AMPK were detected by western blotting. (FIG. 3B and FIG. 3C) Mice received leptin (3 mg/kg) followed at 1 h by clozapine (5 mg/kg) and were sacrificed at 3 h. Phospho-AMPK and total AMPK were detected by western blotting and $\alpha 2$-AMPK activity was assayed. Bars represent the mean±SE of three independent lysates performed in triplicate. (*p<0.001, Student's t-test, n=5)

(FIG. 4A) Hypothalamic slices were incubated with triprolidine (50 or 500 nM) or clozapine (200 nM) for 30 min. Phospho-AMPK and total AMPK were detected by western blotting. (FIG. 4B) Hypothalamic slices were incubated with different concentration of histamine in the absence or presence of 200 nM clozapine for 30 min. Phospho-AMPK and total AMPK were detected by Western blotting. (FIG. 4C) Mice were administered saline or 3 mg/kg clozapine and perfused with 4% paraformaldehyde. Immunohistochemistry was performed with an antibody specific for phospho-AMPK. (FIG. 4D) Quantification of immunohistochemistry. Bars represent the mean±SE of five independent slides. (*p<0.005, **p<0.001 Student's t-test, n=5)

(FIG. 5A) Mice were administered clozapine (1 mg/kg, i.p.) and sacrificed at 3 h. Cerebellum and liver were removed and phosphorylated AMPK (AMPK-P) detected by western blotting. Each lane represents tissue from individual mouse. (FIG. 5B) Mice received clozapine (3 mg/kg, i.p.) and were sacrificed at 3 h. Hypothalamus, cerebellum and liver were removed and phosphorylated AMPK (AMPK-P) detected by western blotting. Each lane represents a tissue from individual mouse. (FIG. 5C and FIG. 5D) Mice were administered clozapine (3 mg/kg i.p.) and sacrificed at 3 h. Hypothalamus and cerebellum were removed and phosphorylated AMPK (AMPK-P) detected by western blotting. Each lane represents a tissue from individual mouse. (FIG. 5E) Mice received clozapine (1 mg/kg, i.p.) and were sacrificed at 24 h. Hypothalami were removed and phosphorylated AMPK (AMPK-P) detected by western blotting. Each lane represents a tissue from an individual mouse. (FIG. 5F) Mice received clozapine (3 mg/kg, i.p.) and were sacrificed at various times. Hypothalami were removed and AMPK activity monitored as described in Material and Methods. Bars represent the mean±SE of three independent lysates performed in triplicate.

(FIG. 7A) Mice received different doses of clozapine and were sacrificed at 3 h. Phosphorylated AMPK was detected by immunohistochemistry. (FIG. 7B) Quantification of data. Bars represent the mean±SE of five independent slides. (*Student's t-test, n=5)

DETAILED DESCRIPTION OF THE INVENTION

Figure 1:
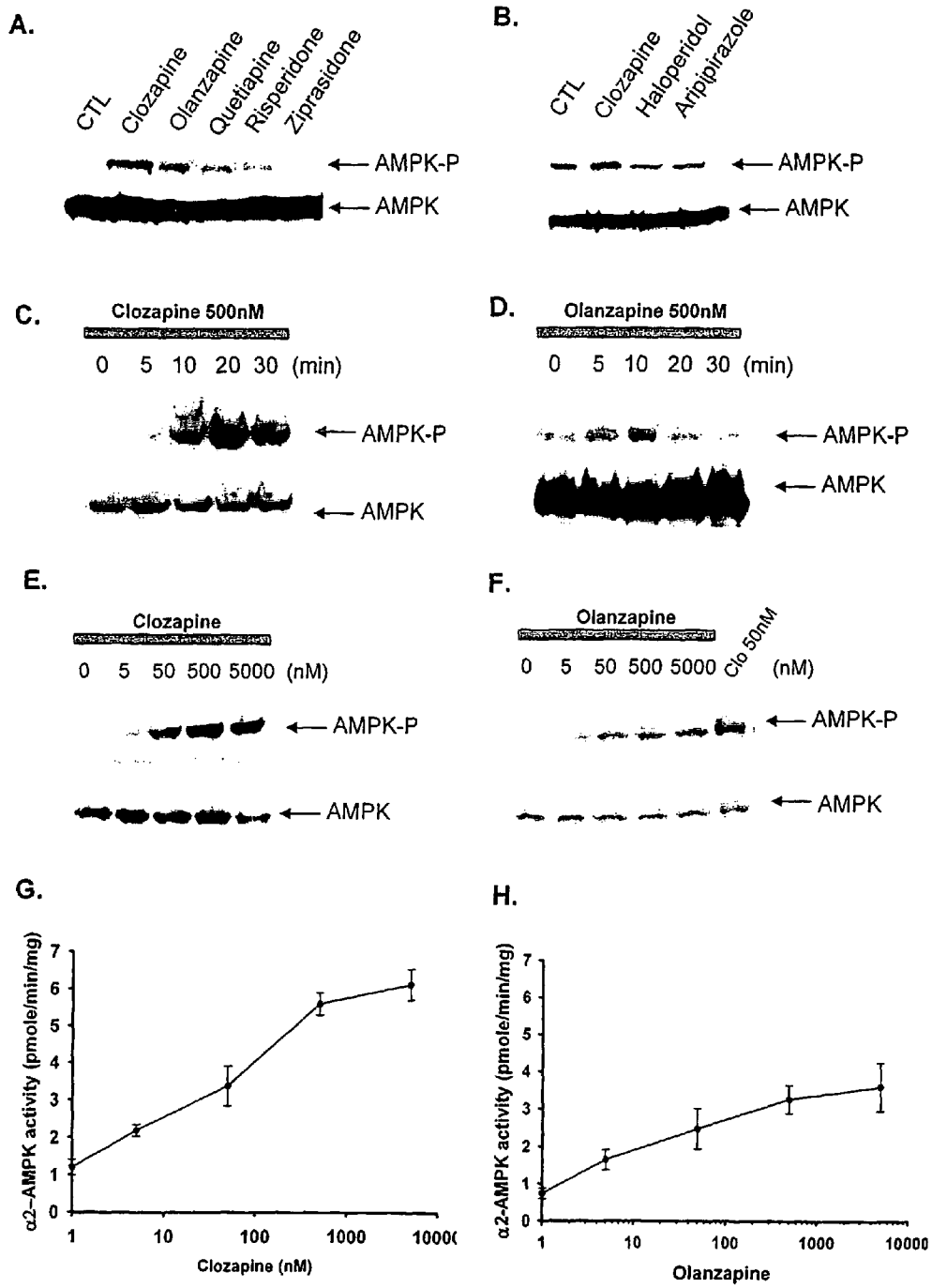
FIGS. 1A-1F. AAPDs activate AMPK in hypothalamic slices.

The inventors have discovered that orexigenic AAPDs potently and selectively stimulate hypothalamic AMP kinase (AMPK). The inventors further demonstrated that orexigenic AAPDs reverse the actions of the anorexigenic hormone leptin. Moreover, the inventors have found that this action involves histamine H1 receptors, as clozapine augmentation of AMPK activity is abolished in H1 receptor knockout mice. In addition, orexigenic potencies of neuroleptics have been found to correlate with their affinities for histamine H1 receptors.

Based on these showings, the inventors have devised methods for testing agents, in particular psychotropic drugs or candidate psychotropic drugs, to predict whether the drugs will be orexigenic. The methods involve testing the agents for their interactions with hypothalamic AMPK and HI receptors. The testing can be done in cell lines, in whole animals, and in cell-free systems.

Psychotropic drugs and candidate psychotropic drugs are those which have proven or suggested psychotropic activity. They can be, for example, approved drugs, under-review drugs, regulated or over-the-counter, neuropleptic or psycholeptic agents, antipsychotic or anti-depressant agents. The testing for orexigenic potential can be performed at any stage in the "life cycle" of a drug, from initial indication of in vitro activity to post-approval or marketing.

Histamine 1 receptors (H1R) can be used in purified form, in cellular membrane preparations, in cloned cells, from any mammalian source, including but not limited to human, rat, dog, mouse, sheep, guinea pig, cow, and pig. Cells or animals which are deficient in HIR, such as knock-out mice can be used as negative controls. One exemplary sequence of HIR which can be used is GenBank Accession No. NP_000852, the disclosure of which is expressly incorporated herein as it exists on the filing date of this application.

Hypothalamic AMPK activity and/or phosphorylation can be measured in slices of hypothalamus from any mammal, including but not limited to human, rat, dog, mouse, sheep, guinea pig, cow, and pig. For scaling up of such measurements, cells of cell lines from hypothalamic sources can be used. The cell lines can similarly be from any mammalian source. Assays for activity or phosphorylation of AMPK can be any that are known in the art. See for example, Y. Minokoshi et al., *Nature* 428, 569 (2004).

Binding to HIR can be determined using any techniques known in the art. Direct binding can be determined or inhibition of a known ligand, such as histamine, can be determined. One or both of the binding partners or the known ligand can be labeled, for example with a radiolabel, a fluorescent label, a chromophore, etc. One of the binding partners can be bound to a solid support during or after the binding reaction to facilitate separation from unbound components. Suitable solid supports are known in the art and any can be used. These include beads, chromatography resin or matrix, polystyrene microwells, etc.

Leptin and insulin are known to reduce AMPK activity. AMPK assays of the present invention can be performed in the presence of leptin and/or insulin. Typically, orexigenic AAPDs are able to reverse the reduction of activity caused by these agents. Other hormones and agents which are known to reduce AMPK activity can be used similarly.

Isogenic pairs of hypothalamic cells can be used to assay for effects on AMPK. The cells may be in animals, such as knock out mice and their wild-type siblings, or the cells may be cultured cells of a continuous cell line. The cells may be of any mammalian species, including mice, rats, guinea pigs, dogs, human, sheep, cows, pigs, etc. Preferably one of the pair of cells is deficient in HIR. More preferably one of the pair of cells is homozygously deficient in HIR. Methods for making homozygous deficient cell lines and knock out mice are well known in the art. See for example, Hogan, B., Beddington, R., Costantini, F. and Lacy, E. (1994) Manipulating the Mouse Embryo: A Laboratory Manual, Cold Spring Harbor Laboratory and the webpage at the Boston University Medical Campus for the Transgenic/Knockout Core Facility, at the page entitled, "Production of Knockout Mice."

According to general methods of laboratory investigation, changes in properties such as activity, binding, and phosphorylation are assessed using statistical measures of significance. There are many statistical measures of significance which can be used in the present invention. Any which are accepted in the scientific community may be used. One such measure which can be used is the Student's t-test. Another is the Chi Square test.

The specific findings described below indicate that the appetite stimulation-weight gain associated with AAPDs is mediated by activation of hypothalamic AMPK following blockade of H1 receptors. AMPK stimulation correlates with the orexigenic actions of the drugs, with clozapine and olanzapine producing the most marked effects. The drug actions are very potent with substantial effects evident at 5 nM concentration. They are selective with effects restricted largely to the arcuate and paraventricular nuclei of the hypothalamus. These findings are consistent with studies implicating central histamine (23, 24) and AMPK (11) in weight control as well as the orexigenic role of the paraventricular and arcuate nuclei (25, 26).

Weight gain elicited by AAPDs can be massive and associated with the "metabolic syndrome" leading to diabetes (5, 7, 27, 28). Thus, the orexigenic actions of AAPDs, especially olanzapine and clozapine, have precluded their use in large numbers of patients. Ignorance of the mechanism of these orexigenic actions has hindered efforts to develop alternative agents. Evaluation of candidate drugs for influences on histamine H1 receptors and hypothalamic AMPK provides a straightforward approach to developing better drugs and may advance our understanding of the hypothalamic regulation of food intake.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

EXAMPLE 1

In hypothalamic slices, clozapine and olazapine markedly enhance levels of phospho-AMPK, and quetiapine, which also is orexigenic, produces similar effects (FIG. 1A). However, risperidone, ziprasidone, haloperidol, and aripipirazole, which are much less orexigenic (Table 1), fail to stimulate AMPK (FIG. 1B). Increased AMPK phosphorylation is observed as early as 5 min after treatment with clozapine or olanzapine (FIGS. 1C and D). The drug actions are potent and substantial with EC50 values for both of about 10 nM and with six and 3.5 fold maximal increases respectively with clozapine and olanzapine (FIGS. 1 E-H).

TABLE 1

| Drugs* | IC50 (nM) | Orexigenic Effects[5,8,14] |
|---|---|---|
| Clozapine | 9 | ++++ |
| Olanzapine | 13 | +++ |
| Quetiapine | 40 | ++ |
| Risperidone | 80 | +/− |
| Ziprasidone | 150 | − |
| Haloperidol | 2000> | − |
| Aripipirazole | 3000> | − |

Neuroleptic affinities for histamine H1 receptors correlate with orexigenic actions. Receptor binding was assayed using rat brain membranes incubated with [$^3$H]mepyramine and 12 concentrations of drugs ranging from 30 pM to 10 µM in triplicate. Data are means of 3 independent determinations which varied less than 10%. Orexigenic action of drugs were obtained from published literatures indicating reproducible differences among AAPDs in eliciting weight gain, when administered at comparable therapeutic doses (5, 8, 14).

Hypothalamic Slices

Hypothalami from 8-10 week old mice were cut at 0.4 mm intervals in sagittal and coronal planes using a McIlwain tissue chopper. The slices were dispersed in artificial cerebrospinal fluid buffer.

Animals

Male C57BL/6 mice (aged 6 weeks) were purchased from Charles River laboratories (Wilmington, Mass.), housed at 22° C., maintained on a 12-h/12-h light/dark cycle, and given access to standard rodent chow and water ad libitum. Experiments were done at age 8-10 weeks. All drugs were administered by i.p. injection. For co-administration experiment, either leptin (3 mg/kg) or insulin (3 mg/kg) were first injected, and at 1 h, clozapine was administered. Procedures were approved by guidelines of the Johns Hopkins University School of Medicine Institutional Animal Care and Use Committee.

Drug Preparation

All drugs were purchased from Toronto Research Chemicals Inc. (Toronto, Canada). Clozapine was dissolved in 0.1 N HCl (0.8 ml) and neutralized by 0.1 N NaOH (0.7 ml). The drug was diluted with 8.5 ml saline solution, and the appropriate doses were administrated to mice. For control mice, the same solution was injected without a drug. For in vitro assays, drugs were dissolved in DMSO.

Kinase Assay

AMPK enzyme activity was assayed as described previously (11). Briefly, hypothalamic slices were maintained at 37° C. in artificial cerebrospinal fluid buffer and treated as indicated in the figure legends. Subsequent to treatment, hypothalamic slices were lysed with AMPK lysis buffer (50 mM Tris.HCl (pH 7.5 at 4° C.), 50 mM NaF, 5 mM Na pyrophosphate, 1 mM EDTA, 1 mM EGTA, 1 mM dithiothreitol, 1 mM benzamidine, 1 mM phenylmethane sulfonyl fluoride, 1% (vol/vol) Triton X-100, and 10% (vol/vol) glycerol by use of a motor-driven pestle. The crude homogenate was sonicated with 4 pulses of 3 s each before centrifugation at 18000 g for 3 min. Protein concentrations were then determined using the Bradford method, and each sample was diluted accordingly to an equivalent protein concentration. To 200 µl of the sample, 2 µl of α-AMPK antibody (Cell Signaling Technologies, Danvers, Mass.) was added, and the immunoprecipitation was incubated overnight at 4° C. with gentle mixing. After 12 h immunoprecipitation, 30 µl of Protein A beads (50% slurry) were added to each sample and incubated for 2 h at 4° C. with gentle mixing. The assay was begun with the addition of immunoprecipitated enzyme to assay buffer (in mM: 80 Hepes buffer, 160 NaCl, 1.6 EDTA, 200 µM SAMS peptide (Alberta Peptide Institute, Edmonton, AB, Canada), 200 µM AMP, 200 µM ATP, 16% glycerol, 0.1% Triton X-100 and 0.5 µCi [γ-$^{32}$P]ATP per sample). After the addition of enzyme to the reaction tube, samples were vortex-mixed for 5 s and incubated for 10 min at 30° C. After incubation, the reaction mixture was vortex-mixed and spotted on P81 Whatman filter paper (Fisher Scientific, Pittsburgh, Pa., U.S.A.), briefly allowed to dry, and washed three times in 1% HClO$_4$ before a single wash in acetone. After sufficient time to allow the filter papers to air dry, samples were immersed in a scintillant-fluor cocktail, and radioactivity was measured in a Beckman scintillation counter. Unless otherwise listed, all reagents used in this assay were purchased from Sigma.

EXAMPLE 2

Figure 2:
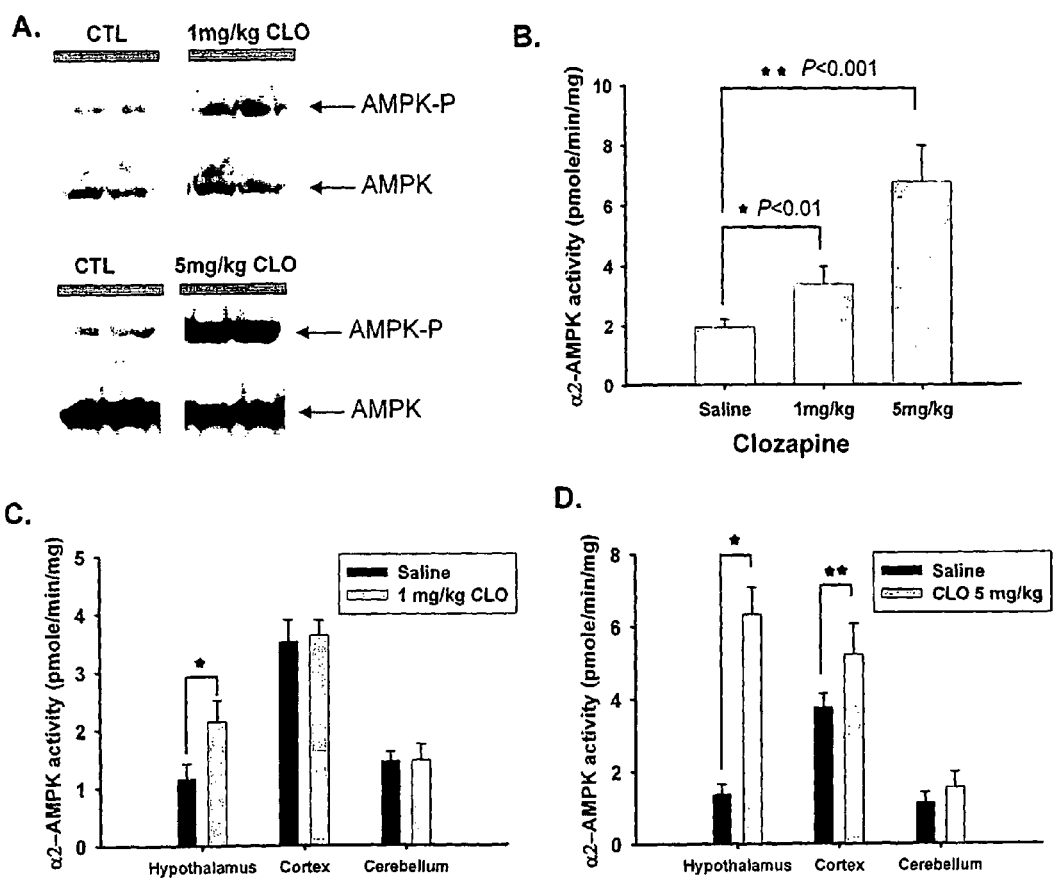
FIGS. 2A-2D. AAPDs activate AMPK in intact animals.
Figure 5:
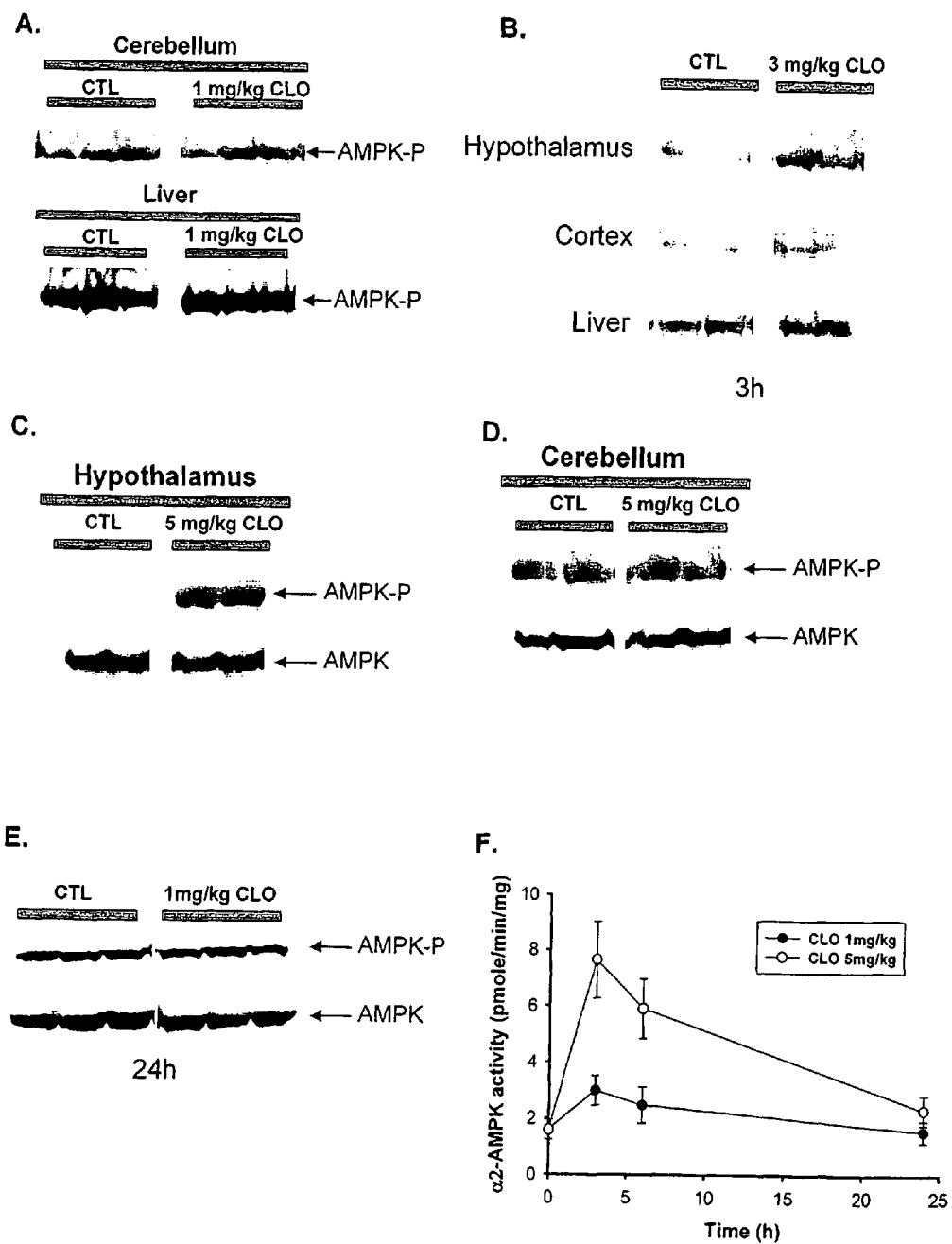
FIGS. 5A-5F. Effect of clozapine on phospho-AMPK is specific to the hypothalamus in intact animals.

Clozapine also potently and selectively augments hypothalamic AMPK in intact animals. As little as 1 mg/kg of clozapine markedly stimulates levels of phospho-AMPK (FIG. 2 A) as well as AMPK catalytic activity with 5 mg/kg producing a 3.5 folds, augmentation of activity (FIG. 2 B). The increase of phospho-AMPK and AMPK catalytic activity is selective for the hypothalamus, as clozapine (1 mg/kg) fails to increase phospho-AMPK levels in the cerebellum and liver (FIGS. 5 A and 5B) and AMPK catalytic activity is not affected in the cerebral cortex or cerebellum by clozapine (1 mg/kg) (FIG. 2 C). At 5 mg/kg, clozapine elicits a 20% increase in cortical AMPK activity, much less than the quadrupling of hypothalamic AMPK activity, while no increase is apparent in the cerebellum (FIG. 2 D). The effect of clozapine is maximal 3 h after drug-administration and gradually decreases to basal levels in 24 h (FIG. 5 F).

EXAMPLE 3

Figure 3:
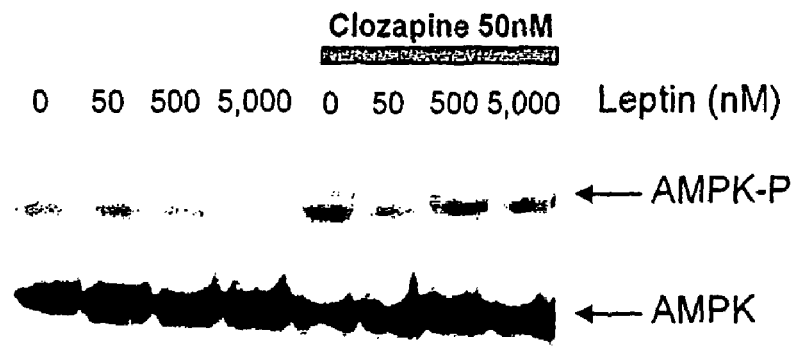
FIGS. 3A-3C. Clozapine reverses effects of leptin on phospho-AMPK in hypothalamic slices and in intact animals.
Figure 3:
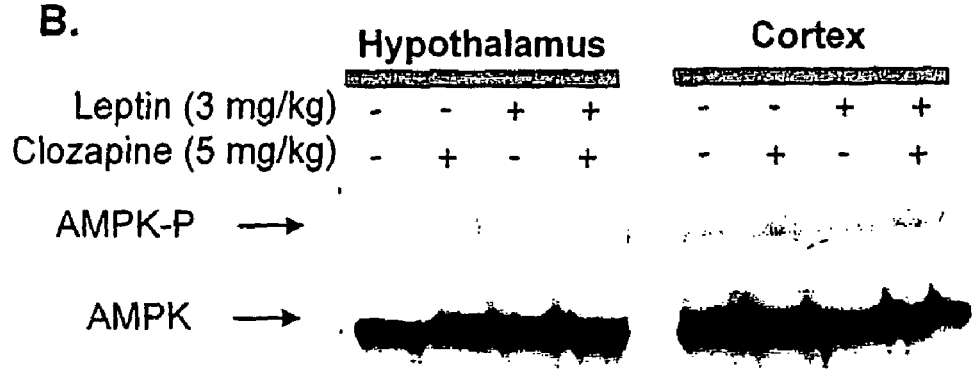
Figure 3:
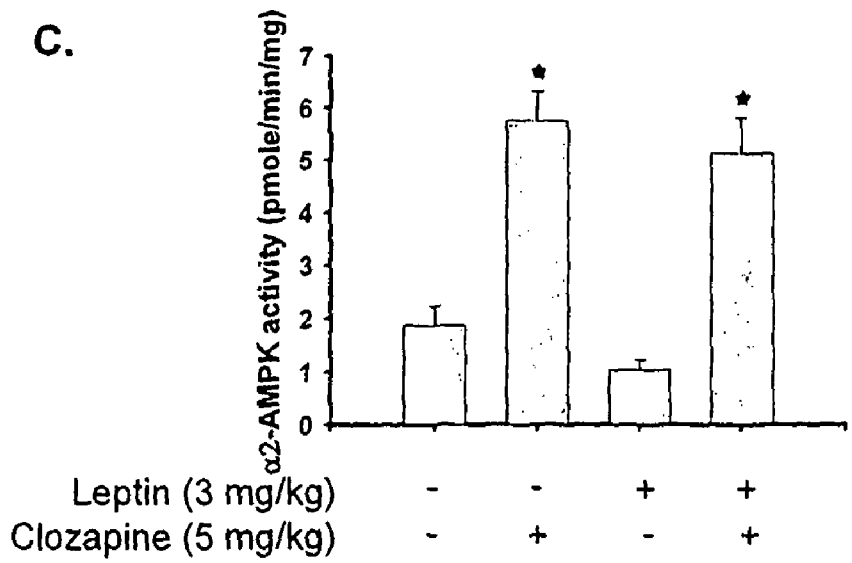
Figure 6:
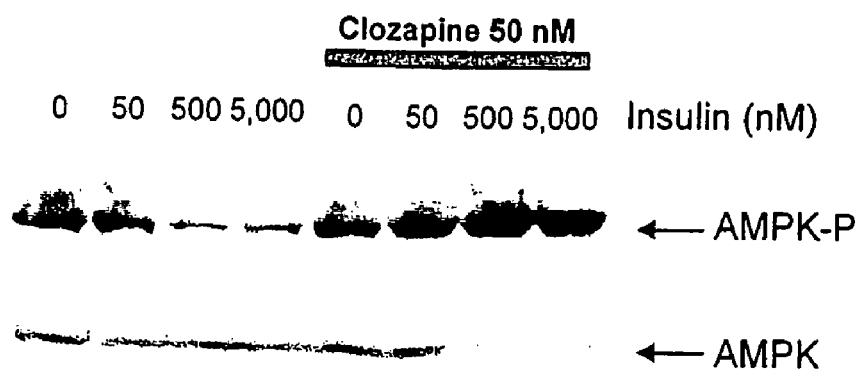
FIG. 6. Clozapine reverses effects of insulin on phospho-AMPK. Hypothalamic slices were treated with various concentrations of insulin in the absence or presence of clozapine (50 mM) for 30 min and phosphorylated AMPK (AMPK-P) detected by western blotting.

Kahn and colleagues (11) reported that the anorexigenic peptide leptin reduces hypothalamic AMPK activity, which we confirm. Clozapine reverses reductions in hypothalamic phospho-AMPK elicited by leptin (FIG. 3 A) and insulin (11) (FIG. 6). In intact mice, leptin (3 mg/kg) reduces hypothalamic phospho-AMPK (FIG. 3 B) and catalytic activity (FIG. 3C), and clozapine reverses these actions.

Figure 7A:
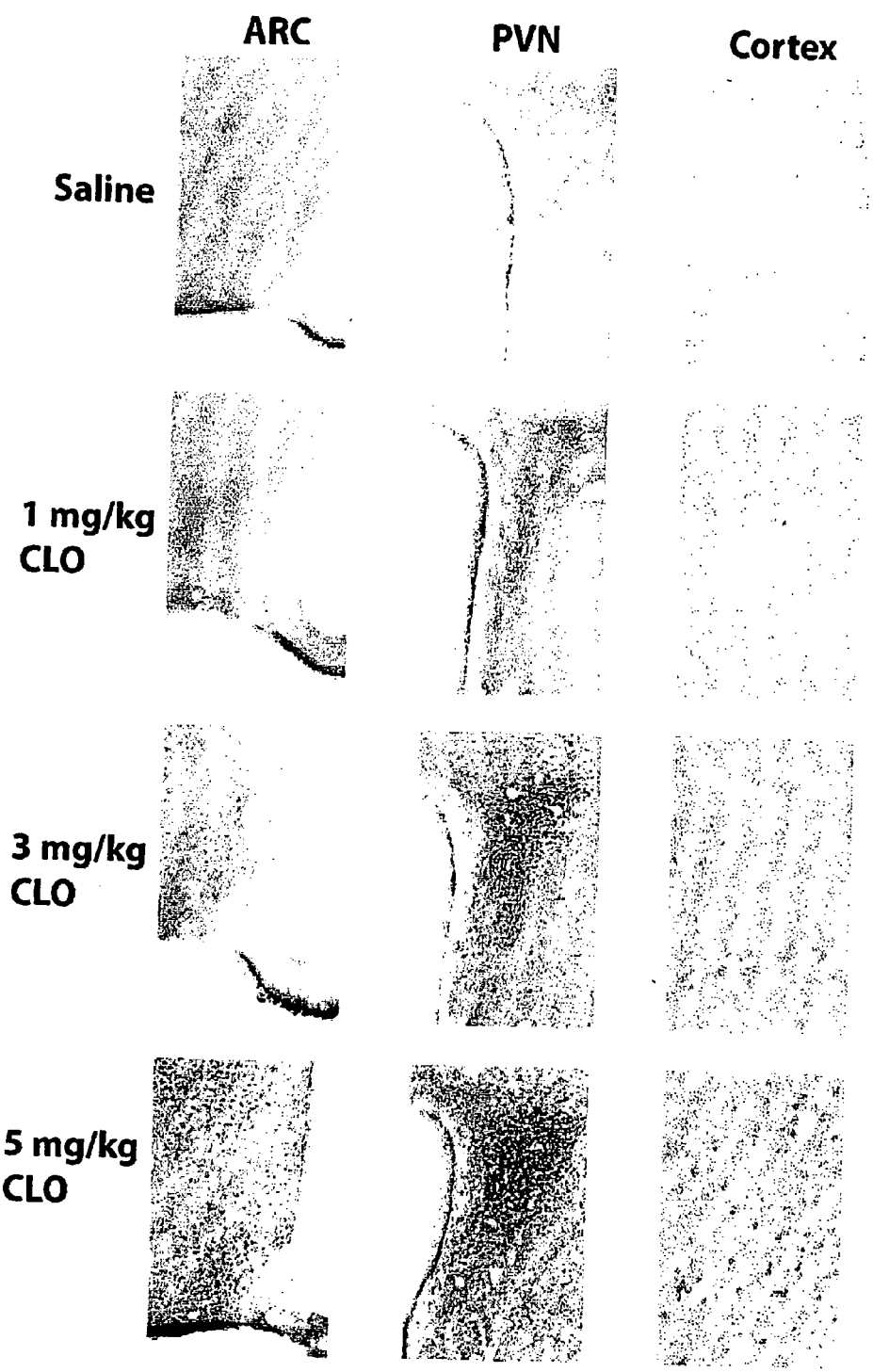
FIGS. 7A-7B. Clozapine effects on phospho-AMPK are specific for the hypothalamus in intact animals.
Figure 7B:
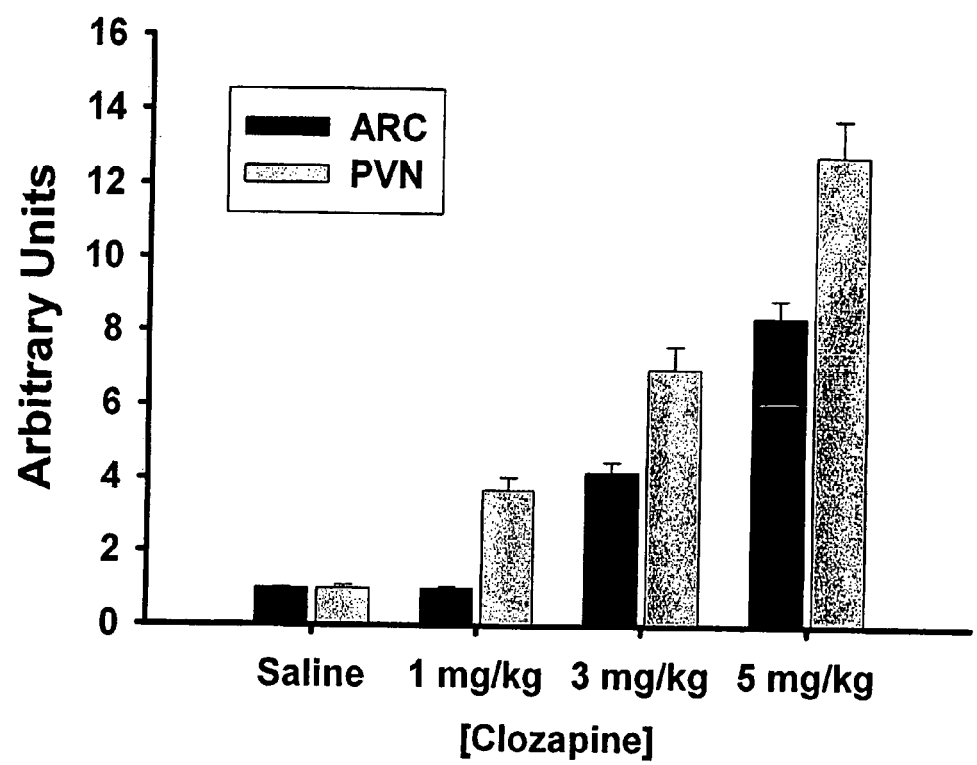
Figure 8:
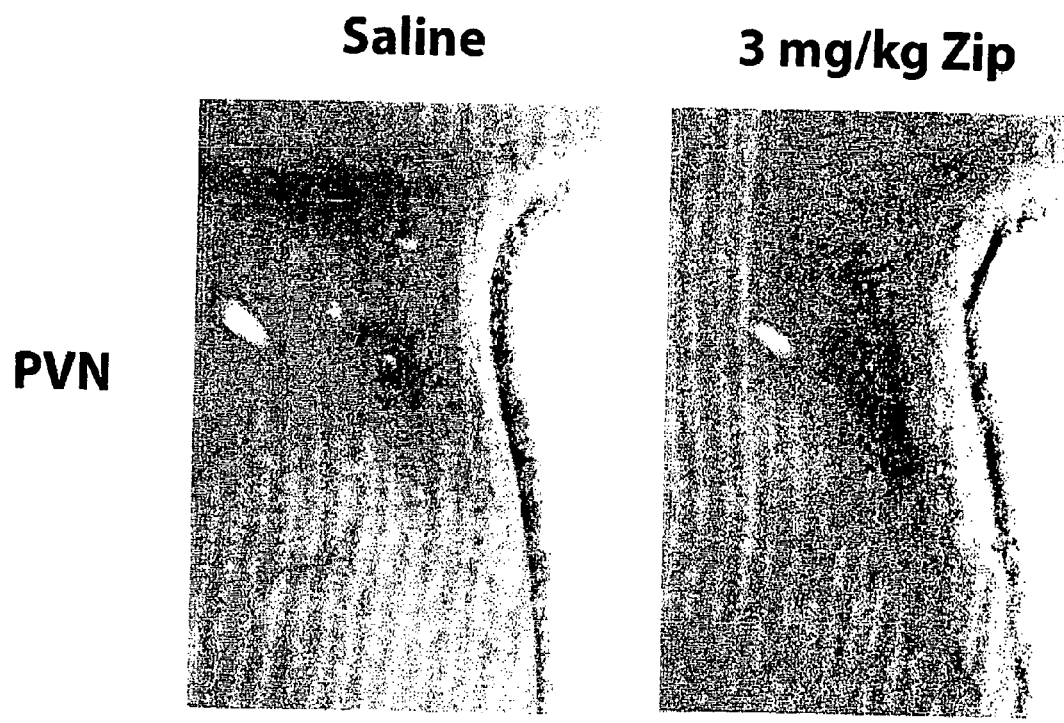
FIG. 8. Ziprasodine has no effect on levels of AMPK-P in intact mouse hypothalamus. Mice received ziprasidone (3 mg/kg, i.p.) and were sacrificed at 3 h. Phosphorylated AMPK was detected by immunohistochemistry.

The arcuate and paraventricular hypothalamic nuclei display the greatest alterations of AMPK activity in response to feeding stimuli (11). In immunohistochemical experiments phospho-AMPK is selectively augmented in these two nuclei with clozapine (1 and 5 mg/kg) while much lesser effects are evident in the cerebral cortex (FIGS. 7A and B). By contrast, ziprasidone fails to alter phospho-AMPK in the paraventricular nucleus (FIG. 8).

Immunohistochemistry

Phospho-AMPKα immunohistochemistry was performed as previously described (E. K. Kim et al., *J. Biol. Chem.* 279, 19970 (2004); A. S. Huang et al., *J. Neurosci.* 26, 2814 (2006)), and all solutions prior to and including the primary antibody incubation contained 2 mM sodium fluoride. C57BL/6 mice or HR1−/− mice (8-10 weeks) were perfused with 4% paraformaldehyde maintained at 37° C. Organs were post-fixed 2 h at room temperature and cryoprotected overnight at 4° C. (30% sucrose in PBS). Free-floating sections (45 μm) were quenched with 3% $H_2O_2$ in water for 10 min at room temperature, washed in TBS-T (16 mM Tris pH 7.4, 140 mM sodium chloride, and 0.1% tween-20), and antigen retrieved for 30 min in a 70° C. water bath (10 mM sodium citrate in TBS-T). Sections were blocked (5% NGS in TBS-T) for 1 h at room temperature and incubated with a mouse anti-phospho-AMPKα antibody (Cell Signaling, Danvers, Mass.) diluted 1:200 into the blocking solution overnight at 4° C. Subsequent washes were conducted in TBST, and labeling was visualized with the Vectastain Elite ABC kit (Vector Laboratories, Burlingame, Calif.). Images were quantified with AlphaEaseFC program.

EXAMPLE 4

We wondered whether the influence of AAPDs on hypothalamic AMPK is secondary to actions of the drugs on specific neuropeptide receptors which have been implicated on appetite regulation. Clozapine and olanzapine (10, 100 nM) fail to influence ligand binding to receptors for leptin, alpha-MSH, and neuropeptide Y (data not shown).

EXAMPLE 5

Figure 4:
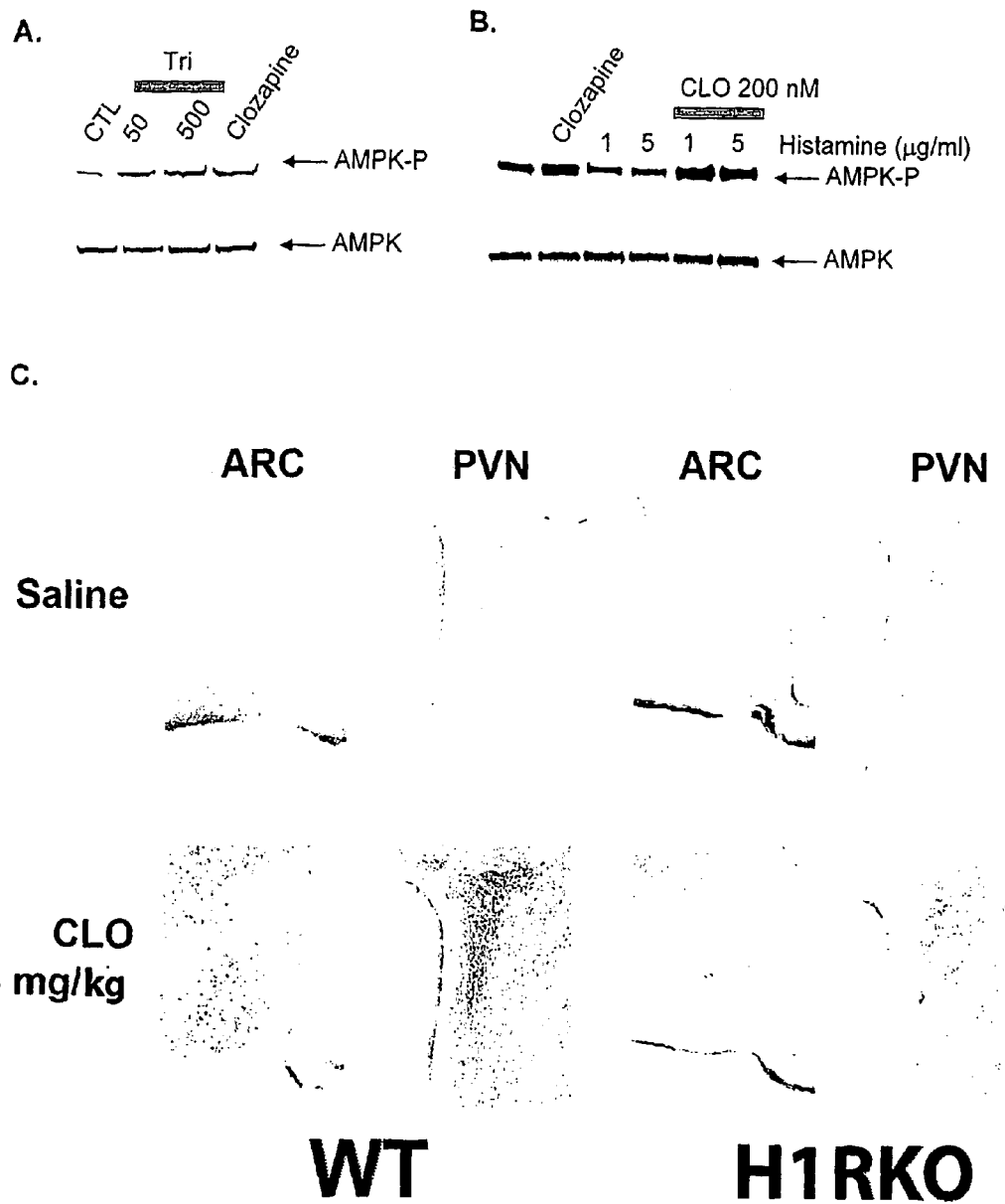
FIGS. 4A-4D. Clozapine activates AMPK through histamine H1 receptors.
Figure 4:
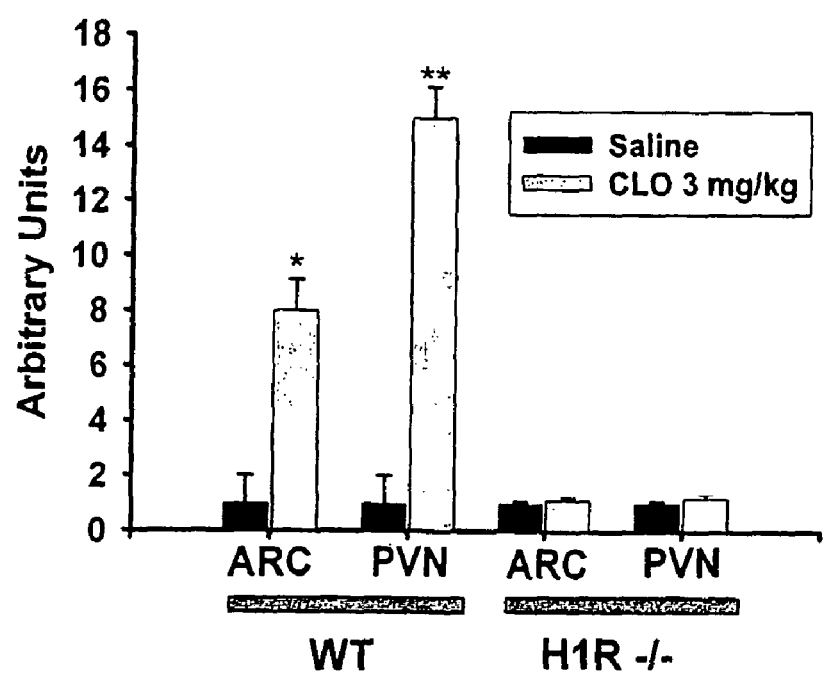
Figure 9:
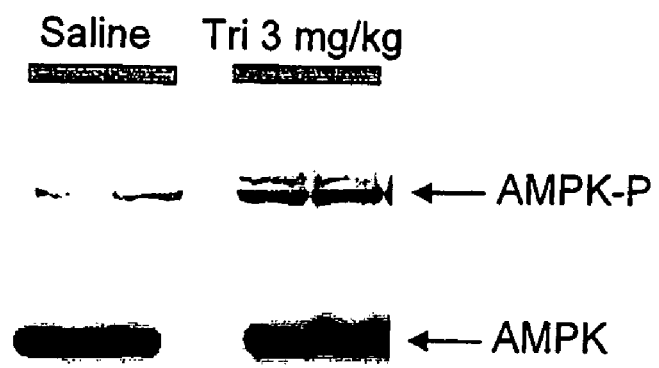
FIG. 9. Triprolidine activates AMPK in intact mouse hypothalamus. Mice received triprolidine (3 mg/kg, i.p.) and were sacrificed at 3 h. Hypothalami were removed and tissue lysates analyzed for AMPK-P by western blotting.

Relative potencies of AAPDs in blocking histamine H1 receptors have been reported to correlate with their orexigenic potencies (21, 22), which we confirm (Table 1). Moreover, in hypothalamic slices the H1 antihistamine triprolidine stimulates phospho-AMPK to the same extent as clozapine both in hypothalamic slices (FIG. 4A) and in intact animals (FIG. 9). Conversely, histamine decreases phospho-AMPK with reversal of this effect by clozapine (FIG. 4B). To explore whether augmentation of phospho-AMPK by drugs stems from H1 receptor blockade, we administered clozapine to H1 receptor deleted mice. Whereas the drug elicits a quadrupling of phospho-AMPK in wild-type mice, no effect is evident in the knockouts (FIGS. 4 C and D).

Effect of Neuroleptics on Histamine H1 Receptor Binding

The IC50 values of neuroleptics on histamine H1 receptors were determined as described previously (R. S. Chang, V. T. Tran, S. H. Snyder, *Eur. J. Pharmacol.* 48, 463 (1978)). Briefly, rats were killed by decapitation and the forebrains removed. Brains were homogenized in 30 vol of Na-K phosphate buffer, pH 7.5, and centrifuged at 48,000×g for 10 min. The tissue was resuspended in buffer and re-centrifuged for an additional 3 times. Tissue was resuspended in buffer at 15 mg/ml.

Tissue (0.2 ml) was added to tubes containing 25 μl of drug and 25 μl of [3H]mepyramine (30 nM). Non-specific binding was determined in the presence of 1 μM triprolidine. Tubes were incubated for 1 h at 25° C., and the samples were filtered over 0.5% poly(ethyleneimine)-coated filters washed with 2×5 ml of cold 50 mM NaCl.

References

The disclosure of each reference cited is expressly incorporated herein.

1. J. Kane, G. Honigfeld, J. Singer, H. Meltzer, *Arch. Gen. Psychiatry* 45, 789 (1988).
2. H. Y. Meltzer, *Hosp. Community Psychiatry* 41, 1356 (1990).
3. R. W. Buchanan, A. Breier, B. Kirkpatrick, P. Ball, W. T. Carpenter, Jr., *Am. J. Psychiatry* 155, 751 (1998).
4. A. Tuunainen, K. Wahlbeck, S. Gilbody, *Schizophr. Res.* 56, 1 (2002).
5. J. A. Lieberman et al., *N. Engl. J. Med.* 353, 1209 (2005).
6. D. Gothelf et al., *Am. J. Psychiatry* 159, 1055 (2002).
7. J. W. Newcomer, *CNS. Drugs* 19 Suppl 1, 1 (2005).
8. D. B. Allison et al., *Am. J. Psychiatry* 156, 1686 (1999).
9. O. Blin, J. Micallef, *J. Clin. Psychiatry* 62 Suppl 7, 11 (2001).
10. M. B. Isaac, M. T. Isaac, *Am. J. Psychiatry* 162, 1764 (2005).
11. Y. Minokoshi et al., *Nature* 428, 569 (2004).
12. J. P. Lindenmayer et al., *Am. J. Psychiatry* 160, 290 (2003).
13. V. L. Albaugh et al., *Obesity.* (Silver. Spring) 14, 36 (2006).
14. D. W. Haupt, *Eur. Neuropsychopharmacol.* (2006).
15. D. G. Hardie, *Annu. Rev. Pharmacol. Toxicol.* (2006).
16. B. B. Kahn, T. Alquier, D. Carling, D. G. Hardie, *Cell Metab* 1, 15 (2005).
17. D. G. Hardie, D. A. Pan, *Biochem. Soc. Trans.* 30, 1064 (2002).
18. D. G. Hardie, S. A. Hawley, J. W. Scott, *J. Physiol* 574, 7 (2006).
19. S. Ramamurthy, G. V. Ronnett, *J. Physiol* 574, 85 (2006).
20. M. J. Wolfgang, M. D. Lane, *Annu. Rev. Nutr.* 26, 23 (2006).
21. W. K. Kroeze et al., *Neuropsychopharmacology* 28, 519 (2003).
22. D. A. Wirshing et al., *J. Clin. Psychiatry* 60, 358 (1999).
23. T. Sakata et al., *Physiol Behav.* 44, 539 (1988).
24. K. Fukagawa et al., *Am. J. Physiol* 256, R605 (1989).
25. M. W. Schwartz, S. C. Woods, D. Porte, Jr., R. J. Seeley, D. G. Baskin, *Nature* 404, 661 (2000).
26. M. A. Cowley et al., *Neuron* 24, 155 (1999).

27. R. N. Bergman, M. Ader, *J. Clin. Psychiatry* 66, 504 (2005).

28. D. E. Casey, *J. Clin. Psychiatry* 65 Suppl 18, 27 (2004).

The invention claimed is:

1. A method of predicting whether an agent which is a psychotropic drug or a candidate psychotropic drug will be orexigenic, comprising the steps of:
   (i) contacting the agent in vitro with a histamine $H_1$ receptor (H1R) and determining if the agent binds to the H1R or contacting the agent in vitro with a histamine $H_1$ receptor (H1R) in the presence of histamine and determining if the agent inhibits histamine binding to the H1R by comparison to a control with no agent;
   (ii) contacting the agent in vitro with a hypothalamic adenosine monophosphate kinase (AMPK) and determining if the agent increases phosphorylation or increases activity of the AMPK by comparison to a control with no agent present; and
   (iii) identifying the agent as likely to be orexigenic when it both (a) binds to H1R or inhibits histamine binding to H1R, and (b) increases phosphorylation of hypothalamic AMPK or increases hypothalamic AMPK activity.

2. The method of claim 1 wherein the step of contacting the agent with a hypothalamic AMPK is performed in the presence of leptin or insulin.

3. The method of claim 1 wherein the agent is an anti-depressant drug or candidate anti-depressant drug.

4. The method of claim 1 wherein the agent is an anti-psychotic drug or candidate anti- psychotic drug.

5. The method of claim 1 wherein the hypothalamic AMPK is in a hypothalamus tissue slice.

6. The method of claim 1 wherein the hypothalamic AMPK is in a hypothalamus cell line.

7. The method of claim 1 wherein the H1R is in a crude mammalian brain membrane preparation.

8. The method of claim 1 wherein the H1R is a cloned, human H1R.

9. The method of claim 1 wherein the agent is contacted with a histamine $H_1$ receptor (H1R) and the binding of the agent to the H1R is determined.

10. The method of claim 1 wherein the agent is contacted with a histamine $H_1$ receptor (H1R) in the presence of histamine and the inhibition of histamine binding to H1R is determined.

11. The method of claim 1 wherein the agent is contacted with a hypothalamic AMPK and an increase in AMPK phosphorylation is determined.

12. The method of claim 1 wherein the agent is contacted with a hypothalamic AMPK and an increase in AMPK activity is determined.

13. The method of claim 1 wherein the agent is contacted with a histamine $H_1$ receptor (H1R) and the binding of the agent to the H1R is determined and the agent is contacted with a hypothalamic AMPK and an increase in AMPK phosphorylation is determined.

14. The method of claim 1 wherein the agent is contacted with a histamine $H_1$ receptor (H1R) and the binding of the agent to the H1R is determined and the agent is contacted with a hypothalamic AMPK and an increase in AMPK activity is determined.

15. The method of claim 1 wherein the agent is contacted with a histamine $H_1$ receptor (H1R) in the presence of histamine and the inhibition of histamine binding to H1R is determined and the agent is contacted with a hypothalamic AMPK and an increase in AMPK phosphorylation is determined.

16. The method of claim 1 wherein the agent is contacted with a histamine $H_1$ receptor (H1R) in the presence of histamine and the inhibition of histamine binding to H1R is determined and the agent is contacted with a hypothalamic AMPK and an increase in AMPK activity is determined.

* * * * *